US007390789B2

(12) United States Patent (10) Patent No.: US 7,390,789 B2
Simmons (45) Date of Patent: Jun. 24, 2008

(54) THIO-CONTAINING INHIBITORS OF AMINOPEPTIDASE P, AND COMPOSITIONS THEREOF

(76) Inventor: William H Simmons, 2842 Denton Ct., Westchester, IL (US) 60154

( * ) Notice: Subject to any disclaimer, the term of this patent is extended or adjusted under 35 U.S.C. 154(b) by 76 days.

(21) Appl. No.: 11/225,748

(22) Filed: Sep. 13, 2005

(65) Prior Publication Data

US 2007/0060525 A1 Mar. 15, 2007

(51) Int. Cl.
*A61K 38/06* (2006.01)
(52) U.S. Cl. .......................................... 514/18; 530/331
(58) Field of Classification Search ....................... None
See application file for complete search history.

(56) References Cited

U.S. PATENT DOCUMENTS

| 4,507,312 | A |   | 3/1985 | Suh et al. |
| 4,549,992 | A |   | 10/1985 | Suh et al. |
| 4,684,660 | A | * | 8/1987 | Ondetti et al. ............... 514/423 |
| 5,508,272 | A |   | 4/1996 | Robl |
| 5,656,603 | A |   | 8/1997 | Simmons |
| 6,777,443 | B2 |   | 8/2004 | Fink |

OTHER PUBLICATIONS

Bagate, K., Develioglu, L., Grima, M., De Jong, W., Simmons, W.H., Imbs, J.-L., Barthelmebs, M. (2000) Vascular catabolism of bradykinin in the isolated perfused kidney. *Eur. J. Pharmacol*, 407, 317-325.
Baxter, G.F., Ebrahim, Z. (2002) Role of bradykinin in preconditioning and protection of the ischaemic myocardium. *Br. J. Pharmacol.* 135, 843-854.
Blais, Jr., C., Marc-Aurele, J., Simmons, W.H., Loute, G., Thibault, P., Skidgel, R.A., Adam, A. (1999) Des-Arg$^9$-bradykinin metabolism in patients who presented hypersensitivity reactions during hemodialysis: role of serum ACE and aminopeptidase P. *Peptides* 20, 421-430.
Coric, P., Turcaud, S., Meudal, H., Roques, B.P., Fournie-Zaluski, M.C. (1996) Optimal recognition of neutral endopeptidase and angiotensin-converting enzyme active sites by mercaptoacyldipeptides as a means to design potent dual inhibitors. *J. Med. Chem.* 39, 1210-1219.
Damas, J., Bourdon, V., Liegeois, J-F., Simmons, W.H. (1996) Influence of several peptidase inhibitors on the pro-inflammatory effects of substance P, capsaicin, and collagenase. *Naunyn-Schmiedeberg's Arch. Pharmacol.* 354, 670-676.
Damas J., Liegois, J.-F., Simmons, W.H. (1996) Potentiation of the pro-inflammatory effects of bradykinin by inhibition of angiotensin-converting enzyme and aminopeptidase P in rat paws. *Naunyn-Schmiedeberg's Arch. Pharmacol.* 354, 670-676.
Dendorfer, A., Wolfrum, S., Wellhöner, P., Korsman, K., Dominiak, P. (1997) Intravascular and interstitial degradation of bradykinin in isolated perfused rat heart. *Br. J.Pharmacol.* 122, 1179-1187.
Dendorfer, A., Wolfrum, S., Schäfer, U., Stewart, J.M., Inamura, N., Dominiak, P. (2000) Potentiation of the vascular response to kinins by inhibition of myocardial kininases. *Hypertension* 35, 32-37.
Dendorfer, A., Folkers, V., Klinger, M., Wolfrum, S., Dominiak, P. (2003) Inhibition of kinin breakdown prolongs retention and action of bradykinin in a myocardial $B_2$ receptor compartment. *Br. J. Pharmacol.* 138, 310-316.
Ersahin, C., Simmons, W.H. (1997) Inhibition of both aminopeptidase P and angiotensin-converting enzyme prevents bradykinin degradation in the rat coronary circulation. *J. Cardiovasc. Pharmacol.* 30, 96-101.
Ersahin, C., Euler, D.E., Simmons, W.H. (1999) Cardioprotective effects of the aminopeptidase P inhibitor apstatin: studies on ischemia/reperfusion injury in the isolated rat heart. *J. Cardiovasc. Pharmacol.* 34, 604-611.
Ersahin, C., Szpaderska, A.M., Simmons, W.H. (2003) Rat and mouse membrane aminopeptidase P: structure analysis and tissue distribution. *Arch. Biochem. Biophys.* 417, 131-140.
Ersahin, C., Szpaderska, A.M., Orawski, A.T., Simmons, W.H. (2005) Aminopeptidase P isozyme expression in human tissues and peripheral blood mononuclear cell fractions. *Arch. Biochem. Biophys.* 435, 303-310.
Fink, C.A., Carlson, J.E., McTaggart, P.A., Qiao, Y., Webb, R., Chatelain, R., Jeng, A.Y., Trapani, A.J. (1996) Mercaptoacyl dipeptides as orally active dual inhibitors of angiotensin-converting enzyme and neutral endopeptidase. *J. Med. Chem.* 39, 3158-3168.
Gainer, J.V., Morrow, J.D., Loveland, A., King, D.J., Brown, N.J. (1998) Effect of bradykinin-receptor blockade on the response to angiotensin-converting-enzyme inhibitor in normotensive and hypertensive subjects. *N. Engl. J. Med.* 339, 1285-1292.
Graham, S.C., Maher, M.J., Simmons, W.H., Freeman, H.C., Guss, M.J. (2004) Structure of *Escherichia coli* aminopeptidase P in complex with the inhibitor apstatin. *Acta Cryst.* D60, 1770-1779.

(Continued)

*Primary Examiner*—Anish Gupta
(74) *Attorney, Agent, or Firm*—Donald Pochopien

(57) ABSTRACT

The present invention is directed to an α thio-containing compound that is capable of inhibiting the enzyme, membrane aminopeptidase P (mAPP or APP), whose natural substrate is bradykinin. The compound is useful as a pharmaceutical agent because by inhibiting bradykinin degradation, the compound allows bradykinin to exert its beneficial effects on the cardiovascular system, to improve renal function, and to improve glucose tolerance and insulin-sensitivity. The present invention is also directed to a pharmaceutical composition comprising the mAPP inhibitor of the present invention and a pharmaceutically acceptable carrier. In another aspect, the present invention is directed to a method of inhibiting bradykinin degradation in a mammalian patient, preferably human, in need of treatment comprising administering to the patient a therapeutically effective amount of an α thio-containing compound of the present invention. The method of the present invention also contemplates the further step of administering to the mammalian patient in need of treatment a therapeutically effective amount of an inhibitor of angiotensin converting enzyme (ACE).

27 Claims, No Drawings

OTHER PUBLICATIONS

Hyde, R.J., Hooper, N.M., Turner, A.J. (1996) Molecular cloning and expression in COS-1 cells of pig kidney aminopeptidase P. *Biochem. J.* 319, 197-210.

Kim, K. Kumar, S., Simmons, W.H., Brown, N.J. (2000) Inhibition of aminopeptidase P potentiates wheal response to bradykinin in angiotensin-converting enzyme inhibitor-treated humans. *J. Pharmacol. Exp. Ther.* 292, 295-298.

Kitamura, S-I., Carbini, L.A., Carretero, O.A., Simmons, W.H., and Scicli, A.G. (1995) Potentiation by [an] aminopeptidase P [inhibitor] of [the] blood pressure response to bradykinin. *Br. J. Pharmacol.* 114, 6-7.

Kitamura, S., Carbini, L.A., Simmons, W.H., Scicli A.G. (1999) Effects of aminopeptidase P inhibition on kinin-mediated vasodepressor responses. *Am. J. Physiol.* 276, H1664-H1671.

Kudoh, A., Kudoh, E., Katagai, H., Takazawa, T. (2001) Effects of the aminopeptidase P inhibitor apstatin on bradykinin-induced inositol 1,4,5-triphosphate in neonatal rat cardiomyocytes. *J. Cardiovasc. Pharmacol,* 37, 495-501.

Leeb-Lundberg, L.M., Marceau, F., Müller-Esterl, W., Pettibone, D.J., Zuraw, B.L. (2005) International Union of Pharmacology. XLV. Classification of the kinin receptor family; from molecular mechanisms to pathophysiological consequences. *Pharmacol. Rev.* 57, 27-77.

Lefebvre, J., Murphey, L.J., Hartert, T.V., Shan R.J., Simmons, W.H., Brown, N.J. (2002) Dipeptidyl peptidase IV activity in patients with ACE-inhibitor-associated angioedema. *Hypertension* 39, 460-464.

Liu, Y., Yang, X., Mehta, D., Bulagannawar, M., Scicli, G.M., Carretero, O.A. (2000) Role of kinins in chronic heart failure and in the therapeutic effect of ACE inhibitors in kininogen-deficient rats. *Am. J. Physiol.* 278, H507-H514.

Loke, K.E., Curran, C.M.L., Messina, E.J., Laycock, S.K., Shesely, E.G., Carretero, O.A., Hintze, T.H. (1999) Role of nitric oxide in the control of cardiac oxygen consumption in $B_2$-kinin receptor knockout mice. *Hypertension* 34, 563-567.

Maggiora, L.L., Orawski, A.T., Simmons, W.H. (1999) Apstatin analog inhibitors of aminopeptidase P, a bradykinin-degrading enzyme. *J. Med. Chem.* 42, 2394-2402.

Molinaro G., Carmona, A.K., Juliano, M.A., Juliano, L., Malitskaya, E., Yessine, M., Chagnon, M., Lepage, Y., Simmons, W.H., Boileau, G., Adam, A. (2005) Human recombinant membrane-bound aminopeptidase P: production of a soluble form and characterization using novel, internally-quenched fluorescent substrates. *Biochem. J.* 385, 389-397.

Moreau, M.E., Garbacki, N., Molinaro, G., Brown, N.J., Marceau, F., Adam, A. (2005) The kallikrein-kinin system: current and future pharmacological targets. *J. Pharmacol. Sci.* 99, 6-38.

Orawski, A.T., Simmons, W.H. (1995) Purification and properties of membrane-bound aminopeptidase P from rat lung. *Biochemistry* 34, 11227-11236.

Orawski, A.T., Susz, J.P. , Simmons, W.H. (1987) Aminopeptidase P from bovine lung: solubilization, properties and potential role in bradykinin degradation. *Mol. Cell. Biochem.* 75, 123-132.

Orawski, A.T., Susz, J.P., Simmons, W.H. (1989) Metabolism of bradykinin by multiple coexisting membrane-bound peptidase in lung: techniques for investigating the role of each peptidase using specific inhibitors. *Adv. Exp. Med. Biol.,* 247B, 355-364.

Pan, H., Chen, S., Scicli, G.M., Carretero, O.A. (2000) Cardiac interstitial bradykinin release during ischemia is enhanced by ischemic preconditioning. *Am. J. Physiol.* 279, H116-H121.

Pretorius, M., Rosenbaum, D., Vaughan, D.E., Brown, N.J. (2003) Angiotensin-coverting enzyme inhibition increases human vascular tissue-type plasminogen activator release through endogenous bradykinin. *Circulation* 107, 579-585.

Prechel, M.M., Orawski, A.T., Maggiora, L.L., Simmons, W.H. (1995) Effect of a new aminopeptidase P inhibitor, apstatin, on bradykinin degradation in the rat lung. *J. Pharmacol. Exp. Thera.* 275, 1136-1142.

Rastegar, M.A., Marchini, F., Morazzoni, G., Végh, A., Papp, J.G., Parratt, J.R. (2000) The effects of Z13752A, a combined ACE/NEP inhibitor, on responses to coronary artery occlusion; a primary protective role for braykinin. *Br. J. Pharmacol.* 129, 671-680.

Robl, J.A., Sun, C.Q., Stevenson, J. et al. (1997) Dual metalloprotease inhibitors: mercaptoacetyl-based fused heterocyclic dipeptide mimetics as inhibitors of angiotensin-converting enzyme and neutral endopeptidase. *J. Med. Chem.* 40, 1570-1577.

Ryan, J.W., Berryer, P., Chung, A.Y.K., Sheffy, D.H. (1994) Characterization of rat pulmonary vascular aminopeptidase P in vivo: role in the inactivation of Bradykinin. *J. Pharmacol. Exp. Thera.* 269, 941-947.

Ryan, J.W., Papapetropoulos, A., Ju, H., Denslow, N.D., Antonov, A., Virmani, R., Kolodgie, F.D., Gerrity, R.G., Catravas, J.D. (1996) Aminopeptidase P is disposed on human endothelial cells. *Immunopharmacol.* 32, 149-152.

Simmons, W.H. (2004) Aminopeptidases P2. In *Handbook of Proteolytic Enzymes*, $2^{nd}$ Ed. (Barrett, A.J., Rawlings, N.D. and Woessner, J.F., eds.), Elsevier Academic Press, London. pp. 934-937.

Simmons, W.H. (2004) Aminopeptidase P (prokaryote). In *Handbook of Proteolytic Enzymes*, $2^{nd}$ *Ed.* (Barrett, A.J., Rawlings, N.D. and Woessner, J.F., eds.), Elsevier Academic Press, London, pp. 928-930.

Simmons, W.H., Orawski, A.T. (1992) Membrane-bound aminopeptidase P from bovine lung: its purification, properties, and degradation of bradykinin. *J. Biol. Chem.* 267, 4897-4903.

Strijtveen, B., Kellogg, R.M. (1986) Synthesis of (racemization prone) optically active thiols by $S_N2$ substitution using cesium thiocarboxylates. *J. Org. Chem.* 51, 3664-3671.

Stöckel-Maschek, A., Stiebitz, B., Koelsch, R., Neubert, K. (2005) Novel 3-amino-2-hydroxy acids containing protease inhibitors. Part 1: synthesis and kinetic characterization as aminopeptidase P inhibitors. *Bioorg. Med. Chem.* 13, 4806-4820.

Subissi, A., Evangelista, S., Giachetti, A. (1999) Preclinical profile of zofenopril: an angiotensin converting enzyme inhibitor with peculiar cardioprotective properties. *Cardiovasc. Drug Rev.* 17, 115-133.

Sulpizio, A.C., Pullen, M.A., Edwards, R.M., Louttit, J.B., West, R., Brooks, D.P. (2005) Mechanism of vasopeptidase inhibitors-induced plasma extravation: comparison of omapatrilat and the novel NEP:ACE inhibitor GW796406. *J. Pharmacol. Exp. Thera.* (Online, Sep. 6, 2005, DOI:10.1124/jpet.105.084749.

Taylor-McCabe, K.J., Ersahin, C., Simmons, W.H. (2001) Bradykinin metabolism in the isolated perfused rabbit heart. *J. Hypertens.* 19, 1295-1299.

Veeravalli, K.K., Akula, A., Routhu, K.V., Kota, M.K. (2003) Infarct size limiting effect of apstatin alone and in combination with enalapril, lisinopril and ramiprilat in rats with experimental myocardial infarction. *Pharmacol. Res.* 48, 557-563.

Veeravalli, K.K., Akula, A. (2004) Involvement of nitric oxide and prostaglandins pathways in the cardioprotective actions of bradykinin in rats with experimental myocardial infarction. *Pharmacol. Res.* 49, 23-29.

Wolfrum, S., Richardt, G., Dominiak , P., Katus, H.A., Dendorfer, A. (2001) Apstatin, a selective inhibitor of aminopeptidase P, reduces myocardial infarct size by a kinin-dependent pathway. *Br. J. Pharmacol.* 134, 370-374.

Yoshimoto, T., Orawski, A.T., Simmons, W.H. (1994) Substrate specificity of aminopeptidase P from *Escherichia coli*: comparison with membrane-bound forms from rat and bovine lung. *Arch. Biochem. Biophys.* 311, 28-34.

Zhang, X., Recchia, F.A., Bernstein, R., Xu, X., Nasjletti, A., Hintze, T.H. (1999) Kinin-mediated coronary nitric oxide production contributes to the therapeutic action of angiotensin-converting enzyme and neutral endopeptidase inhibitors and amlodipine in the treatment in heart failure. *J. Pharmacol. Exp. Thera.* 288, 742-751.

Nagpal J, Gogia S: "Racecadotril." *Indian Pediatr*. 2004:1218-1224.

Takeyama K, Minato H, Fukuya F, Kawahara S, Hosoki K, Kadodawa T: Antihypertensive activity of alacepril, an orally active angiotensin converting enzyme inhibitor, in renal hypertensive rats and dogs. *Arzneimittelforschung* 1985; 10:1502-1507.

Trapani AJ, Beil ME, Bruseo CW, Fink CA, Hoyer D, Savage P, Jeng AY: "Effects of the ECE/NEP inhibitor CGS 34225 on the big ET-1-induced pressor response and plasma atrial natriuretic peptide concentration in concious rats." *Clin. Sci.* 2002; 103(Suppl. 48):1025-1065.

* cited by examiner

THIO-CONTAINING INHIBITORS OF AMINOPEPTIDASE P, AND COMPOSITIONS THEREOF

BACKGROUND OF THE INVENTION

The present invention is directed to a thio-containing compound that is capable of inhibiting the enzyme, membrane aminopeptidase P (mAPP or APP), whose natural substrate is bradykinin. The compound is useful as a pharmaceutical agent because by inhibiting bradykinin degradation, the compound allows bradykinin to exert its beneficial effects on the cardiovascular system (including decreasing blood pressure, dilating coronary arteries, providing protective effects on the heart during myocardial ischemia/reperfusion injury, and stimulating formation of new blood vessels), to improve renal function, and to improve glucose tolerance and insulin-sensitivity. The present invention is also directed to a pharmaceutical composition comprising the mAPP inhibitor of the present invention and to a method of inhibiting bradykinin degradation in a mammalian patient, particularly a human patient.

Cardiovascular diseases account for 38% of all deaths in the United States. The most prevalent cardiovascular disorder is hypertension, which currently afflicts 50 million people. Although there has been an improvement in the percentage of hypertensive individuals who are aware of their condition and are being treated, only half of those treated (just 31% of all hypertensives) actually have their blood pressure under control. The difficulty of treating hypertension is evidenced by the fact that more than two-thirds of hypertensive patients require two or more drugs to achieve blood pressure control. Consequently, the development of a new class of drugs will provide additional therapeutic options that can reduce the burden of hypertension and its sequelae.

In addition, more than a million persons in the U.S. have a heart attack each year, resulting in over 500,000 deaths. New medications are needed that can prevent and treat acute myocardial infarction.

One option for treating cardiovascular diseases is to increase the body's concentration of the hormone bradykinin. Bradykinin is known to decrease blood pressure and to protect the heart from ischemic damage. However, this hormone has limited beneficial effects because it is rapidly degraded by aminopeptidase P and angiotensin-converting enzyme (ACE). The ACE inhibitor drugs can potentiate bradykinin by inhibiting its degradation. Some of the blood pressure lowering effects and most of the acute cardioprotective effects of ACE inhibitors are due to this mechanism. Angiotensin II receptor antagonists also act in part through bradykinin, since they increase the activation of the $AT_2$ receptor, which in turn stimulates bradykinin release from endothelial cells.

A novel alternative method was devised for increasing bradykinin levels, namely, inhibiting aminopeptidase P (U.S. Pat. No. 5,656,603; William H. Simmons, Ph.D., inventor; Loyola University Chicago, assignee). The prototype aminopeptidase P inhibitor, apstatin (Formula I), was shown to reduce bradykinin degradation in the isolated perfused rat heart and lung. Apstatin enhanced the blood pressure-lowering

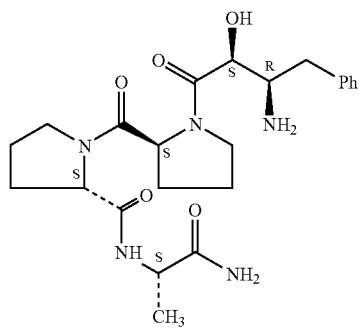

effects of intravenously administered bradykinin. In a rat model of severe hypertension, apstatin acted synergistically with an ACE inhibitor to reduce blood pressure to normal. [Kitamura et al. "Effects of aminopeptidase P inhibition on kinin-mediated vasodepressor responses," Am. J. Physiol., 276, H1664-H1671 (1999)] mAPP inhibition with apstatin also exhibited cardioprotective effects; in a heart attack model using an isolated perfused heart, apstatin reduced cardiac damage by 74%. [Ersahin et al., "Cardioprotective effects of the aminopeptidase P inhibitor apstatin: studies on ischemia/reperfusion injury in the isolated rat heart," J. Cardiovasc. Pharmacol., 34, 604-611 (1999)] It reduced reperfusion-induced ventricular fibrillation by a similar amount. Subsequent studies in other laboratories showed that inhibiting mAPP by administering apstatin substantially reduced myocardial infarct size in intact rats subjected to regional cardiac ischemia. [Wolfrum et al., "Apstatin, a selective inhibitor of aminopeptidase P, reduces myocardial infarct size by a kinin-dependent pathway," Br. J. Pharmacol., 134, 370-374 (2001); Veeravalli et al., "Infarct size limiting effect of apstatin alone and in combination with enalapril, lisinopril and ramiprilat in rats with experimental myocardial infarction," Pharmacol. Res., 48, 557-563 (2003)]

Apstatin has excellent pharmacological properties, exhibits reasonable potency (micromolar), and has good specificity and metabolic stability. However, it has chemical properties that limit its usefulness as an orally active drug. Although apstatin and related compounds have potential as injectable drugs, the potency and predicted intestinal absorption rate are probably too low to allow them to be effective following oral administration. Therefore, it is an object of the present invention to discover mAPP inhibitors having greater potency (i.e., a lower $IC_{50}$) than apstatin such that they can be administered in lower dosages as injectable drugs, and/or that because of their potency and chemical structure can be administered in an orally acceptable form.

BRIEF SUMMARY OF THE INVENTION

The applicants have discovered a novel compound that exhibits a greatly enhanced inhibition of mAPP. Thus, in its first aspect, the present invention is directed to a compound of formula III:

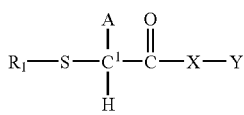

wherein C¹ is of configuration S or R;
wherein R₁ is hydrogen, methyl, or

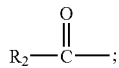

wherein A is a hydrogen, straight or branched chain lower alkyl having 1 to 8 carbon atoms, straight or branched chain lower alkenyl or alkynyl having 2 to 8 carbon atoms, cyclic alkyl or alkenyl having 4 to 8 carbon atoms, phenyl, or benzyl;

wherein X is (L)-prolyl, 3,4-dehydro-(L)-prolyl, (2S,3R)-3-methylpyrrolidine-2-carbonyl, (2S,5R)-5-methylpyrrolidine-2-carbonyl, (S)-piperidine-2-carbonyl, or (R)-thiazolidine-4-carbonyl;

wherein Y is an amino acid or a dipeptide, where in the dipeptide the first (N-terminal) amino acid is (L)-prolyl, 3,4-dehydro-(L)-prolyl, (2S,3R)-3-methylpyrrolidine-2-carbonyl, (2S,3S)-3-methylpyrrolidine-2-carbonyl, (2S,4R)-4-methylpyrrolidine-2-carbonyl, (2S,4S)-4-methylpyrrolidine-2-carbonyl, (2S,5R)-5-methylpyrrolidine-2-carbonyl, (2S,4R)-4-hydroxypyrrolidine-2-carbonyl, (2S,4S)-4-hydroxypyrrolidine-2-carbonyl, (S)-piperidine-2-carbonyl, or (R)-thiazolidine-4-carbonyl, and the second (C-terminal) amino acid is (L)-alanyl, (L)-prolyl, sarcosyl, an (S or R) N-methyl amino acid with a hydrophobic side chain, β-alanine, or other β-amino acid with a hydrophobic side chain, or a D-amino acid with a hydrophobic side chain; and wherein Y further has a carboxyl, carboxyamide, or a —COOR₂ moiety at its carboxyl terminus;

R₂ is alkyl or substituted alkyl having 1-6 carbon atoms; alkenyl or substituted alkenyl having 2-6 carbon atoms; or cycloalkyl-(CH₂)ₐ—, aryl-(CH₂)ₐ—, substituted aryl-(CH₂)ₐ—, or heteroaryl-(CH₂)ₐ—, having 4-12 carbon atoms; and a is zero or an integer from 1 to 6. Typically, a is 1 or 2. More typically, a is 1.

Preferably, the present invention is directed to a compound of Formula III:

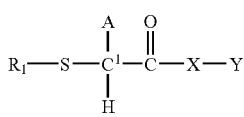

wherein C¹ is of configuration S or R;
wherein R₁ is hydrogen or R₂CO—;
wherein A is straight or branched chain alkyl of 1-6 carbon atoms, or cyclic alkyl or alkenyl having 4 to 8 carbon atoms;
wherein X is (L) prolyl;
wherein Y is a dipeptide wherein the first (N-terminal) amino acid is (L) prolyl, and the second (C-terminal) amino acid is (L)-alanyl or β-alaninyl, or a one to six carbon alkyl- or aryl ester thereof; or (L)-alanyl amide or β-alaninyl amide;

R₂ is alkyl or substituted alkyl, having 1-6 carbon atoms; or cycloalkyl-(CH₂)ₐ—, aryl-(CH₂)ₐ—, substituted aryl-(CH₂)ₐ—, or heteroaryl-(CH₂)ₐ—, having 4-12 carbon atoms; and a is zero or an integer from 1 to 2.

More preferably, the present invention is directed to a compound of Formula III:

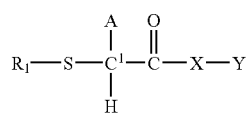

wherein C¹ is of configuration S or R;
wherein R₁ is hydrogen or R₂CO—;
wherein A is straight or branched chain alkyl of 1-6 carbon atoms;
wherein X is (L) prolyl;
wherein Y is a dipeptide wherein the first (i.e., N-terminal) amino acid is (L) prolyl, and the second (i.e., C-terminal) amino acid is (L)-alanyl or β-alaninyl, or (L)-alanyl amide or β-alaninyl amide;
R₂ is alkyl or substituted alkyl having 1-6 carbon atoms.

Most preferably, the present invention is directed to a compound of formula VIII:

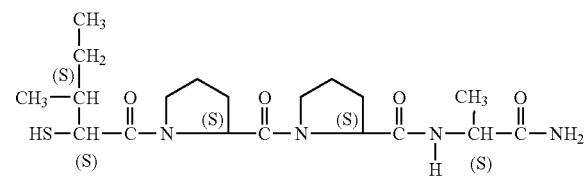

In its second aspect, the present invention is directed to a pharmaceutical composition comprising in combination a therapeutically effective amount of the active APP inhibitor (compound) of the present invention, as defined herein, and a pharmaceutically acceptable carrier.

In its third aspect, the present invention is directed to a method of inhibiting bradykinin degradation in a mammalian patient, preferably a human patient, in need of treatment comprising administering to the patient a therapeutically effective amount of a an APP inhibitor (compound) of the present invention in a first pharmaceutically effective carrier.

In another aspect, the present invention is directed to a method for treating hypertension in a mammalian patient, preferably a human patient, in need of treatment comprising administering a therapeutically effective amount of a compound of the present invention in a first pharmaceutically acceptable carrier.

In yet another aspect, the present invention is directed to a method for dilating the coronary arteries in a mammalian patient, preferably a human patient, in need of treatment comprising administering a therapeutically effective amount of a compound of the present invention in a first pharmaceutically acceptable carrier.

In yet another aspect, the present invention is directed to a method for enhancing renal function in a mammalian patient, preferably a human patient, in need of treatment comprising administering a therapeutically effective amount of an compound of the present invention in a first pharmaceutically acceptable carrier.

In a second embodiment of each the above methods, the method includes the step of administering to said patient a therapeutically effective amount of an inhibitor of angiotensin converting enzyme in a second pharmaceutically acceptable carrier. The first pharmaceutically acceptable carrier for the compound (APP inhibitor) of the present invention, and the second pharmaceutically acceptable carrier for the inhibitor of ACE may be the same or different.

The inhibitor of ACE is typically one or more members selected from the group of inhibitors of ACE consisting of captopril, enalapril, enalaprilat, lisinopril, quinapril, benazepril, fosinopril, ramipril and ramiprilat. Preferably, the inhibitor of ACE is one or more members selected from the group of inhibitors of ACE consisting of ramipril and ramiprilat.

DETAILED DESCRIPTION OF THE INVENTION

The present invention has multiple embodiments. In its first embodiment, the present invention is directed to a compound of formula III:

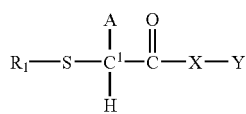

III wherein $C^1$ is of configuration S or R;
wherein $R_1$ is hydrogen, methyl, or

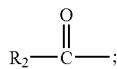

wherein A is a hydrogen, straight or branched chain lower alkyl having 1 to 8 carbon atoms, straight or branched chain lower alkenyl or alkynyl having 2 to 8 carbon atoms, cyclic alkyl or alkenyl having 3 to 8 carbon atoms, phenyl, or benzyl;
wherein X is (L)-prolyl, 3,4-dehydro-(L)-prolyl, (2S,3R)-3-methylpyrrolidine-2-carbonyl, (2S,5R)-5-methylpyrrolidine-2-carbonyl, (S)-piperidine-2-carbonyl, or (R)-thiazolidine-4-carbonyl;
wherein Y is an amino acid or a dipeptide, where in the dipeptide the first N-terminal amino acid is (L)-prolyl, 3,4-dehydro-(L)-prolyl, (2S,3R)-3-methylpyrrolidine-2-carbonyl, (2S,3S)-3-methylpyrrolidine-2-carbonyl, (2S,4R)-4-methylpyrrolidine-2-carbonyl, (2S,4S)-4-methylpyrrolidine-2-carbonyl, (2S,5R)-5-methylpyrrolidine-2-carbonyl, (2S,4R)-4-hydroxypyrrolidine-2-carbonyl, (2S,4S)-4-hydroxypyrrolidine-2-carbonyl, (S)-piperidine-2-carbonyl, or (R)-thiazolidine-4-carbonyl, and the second amino acid is (L)-alanyl, (L)-prolyl, sarcosyl, an (S, or R) N-methyl amino acid with a hydrophobic side chain, β-alanine, or other β-amino acid with a hydrophobic side chain, or a D-amino acid with a hydrophobic side chain; and wherein Y further has a carboxyl, carboxyamide, or a —$COOR_2$ moiety at its carboxyl terminus;
$R_2$ is alkyl or substituted alkyl having 1-6 carbon atoms, alkenyl or substituted alkenyl having 2-6 carbon atoms, cycloalkyl-$(CH_2)_a$—, aryl-$(CH_2)_a$—, substituted aryl-$(CH_2)_a$—, or heteroaryl-$(CH_2)_a$—; and
a is zero or an integer from 1 to 6. Typically, a is 1 or 2. More typically, a is 1.

As used herein, the terms "alkyl" or "lower alkyl" refer to a straight chain or branched chain hydrocarbon radical having from about 1 to about 8 carbon atoms, and more preferably 1 to about 6 carbon atoms. Examples of such alkyl radicals are methyl, ethyl, n-propyl, isopropyl, n-butyl, isobutyl, sec-butyl, t-butyl, pentyl, neopentyl, hexyl, isohexyl, and the like.

As used herein, the terms "alkenyl" or "lower alkenyl" refer to unsaturated acyclic hydrocarbon radicals containing at least one double bond and 2 to about 6 carbon atoms, which carbon-carbon double bond may have either cis or trans geometry within the alkenyl moiety, relative to groups substituted on the double bond carbons. Examples of such radicals (groups) are ethenyl, propenyl, butenyl, isobutenyl, pentenyl, isopentenyl, hexenyl and the like.

As used herein, the terms "alkynyl" or "lower alkynyl" refer to acyclic hydrocarbon radicals containing one or more triple bonds and 2 to about 6 carbon atoms. Examples of such radicals (groups) are ethynyl, propynyl, butynyl, pentynyl, hexynyl and the like.

The term "cycloalkyl" as used herein means saturated or partially unsaturated cyclic carbon radicals containing 3 to about 8 carbon atoms and more preferably 4 to about 6 carbon atoms. Examples of such cycloalkyl radicals (groups) include cyclopropyl, cyclopropenyl, cyclobutyl, 1-cyclobuten-1-yl, 1-cyclobuten-2-yl, cyclopentyl, cyclohexyl, 2-cyclohexen-1-yl, and the like.

The term "aryl" as used herein denotes aromatic ring systems composed of one or more aromatic rings. Preferred aryl groups are those consisting of one, two or three aromatic rings. More preferably, the aryl group has a single ring. The term "aryl" embraces aromatic radicals such as phenyl, pyridyl, naphthyl, thiophene, furan, biphenyl and the like.

The term "hydrophobic side chain" as used herein is meant an aliphatic or aromatic side chain of 1-10 carbon atoms. The aliphatic side chain is straight, branched or cyclic, and is alkyl, alkenyl or alkynyl. Preferably, the hydrophobic side chain is unsubstituted and lacks a hydroxy or amino group. The term "aromatic side chain" includes pure aromatic compounds and alkyl substituted aromatic compounds.

The term "substituted alkyl" as used herein means straight or branched chain lower alkyl having 1 to 8 carbon atoms, preferably 1-6 carbon atoms, and substituted with one or more members selected from the group consisting of: hydroxy, amino, fluoro, chloro, bromo, iodo, —COOH, and —COOZ; wherein Z is a pharmaceutically acceptable cation.

The term "substituted aryl" is meant "aryl" as defined above substituted with one or more members selected from the group consisting of: hydroxy, amino, fluoro, chloro, bromo, iodo, —COOH, and —COOZ; wherein Z is a pharmaceutically acceptable cation as already described herein.

By the term "heteroaryl" is meant aryl with 1-2 heteroatoms, i.e., 1-2 atoms other than carbon, such as N, O, or S. When there are two heteroatoms, they may be the same or different.

The terms "hydroxy" and "hydroxyl" as used herein are synonymous and are represented by a radical of the formula: —OH.

Preferably, the present invention is directed to a compound of Formula III:

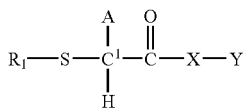

wherein $C^1$ is of configuration S or R;
wherein $R_1$ is hydrogen or $R_2CO$—;
wherein A is straight or branched chain alkyl of 1-6 carbon atoms, or cyclic alkyl or alkenyl having 4 to 8 carbon atoms;
wherein X is (L) prolyl;
wherein Y is a dipeptide wherein the first (N-terminal) amino acid is (L) prolyl, and the second (C-terminal) amino acid is (L)-alanyl or β-alaninyl, or a one to six carbon alkyl- or aryl ester thereof; or (L)-alanyl amide or β-alaninyl amide;
$R_2$ is alkyl or substituted alkyl, having 1-6 carbon atoms; or $R_2$ is cycloalkyl-$(CH_2)_a$—, aryl-$(CH_2)_a$—, substituted aryl-$(CH_2)_a$—, or heteroaryl-$(CH_2)_a$—, having 4-12 carbon atoms; and
a is zero or an integer from 1 to 6.

More preferably, the present invention is directed to a compound of Formula III:

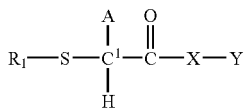

wherein $C^1$ is of configuration S or R;
wherein $R_1$ is hydrogen or $R_2CO$—;
wherein A is straight or branched chain alkyl of 1-6 carbon atoms;
wherein X is (L) prolyl;
wherein Y is a dipeptide wherein the first (N-terminal) amino acid is (L) prolyl, and the second (C-terminal) amino acid is (L)-alanyl or β-alaninyl, or (L)-alanyl amide or β-alaninyl amide;
$R_2$ is alkyl or substituted alkyl, having 1-6 carbon atoms.

Representative compounds of the invention include the compounds of formulas IV-VIII. Preferred compounds of the invention include the compounds of formulas V-VIII:

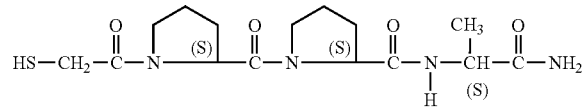

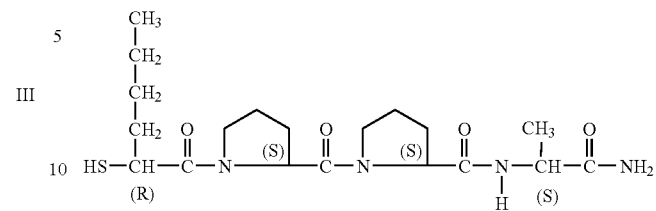

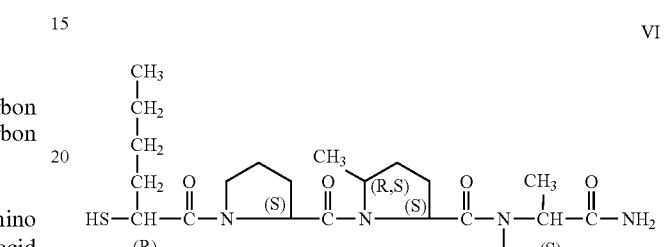

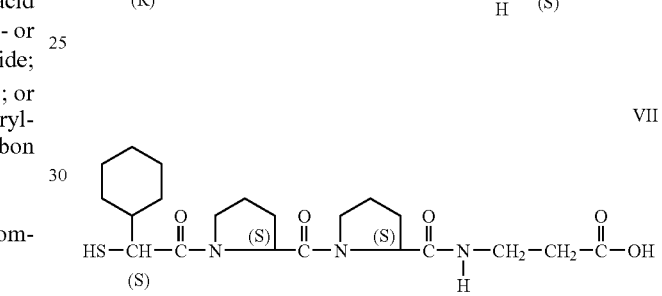

or

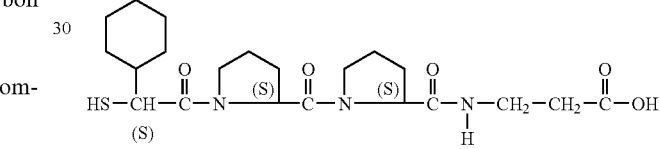

A method for the preparation of each of the compounds of formulas IV-VIII is disclosed in the Examples herein.

Most preferably, the present invention is directed to a compound of formula VIII:

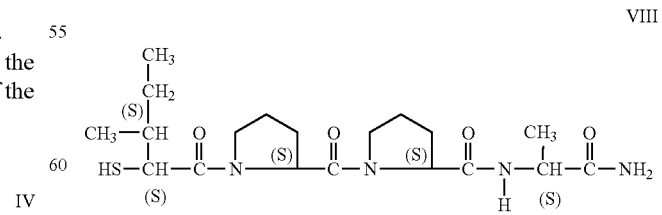

The $IC_{50}$ for each of compounds IV-VIII was determined as the concentration in nmoles/liter (nM) required to inhibit rat membrane aminopeptidase P by 50% using Arg-Pro-Pro (0.5 mM) as the substrate. Rat mAPP has been shown to be an acceptable alternate for human, monkey and bovine mAPP and to have a statistically significant correlation with these other mAPP, particularly human APP. See Maggiora et al.,

TABLE 1

| Analog | Formula | Structure | Binding affinity ($IC_{50}$ in nanomolar)[1] |
|---|---|---|---|
| 1 | IV | 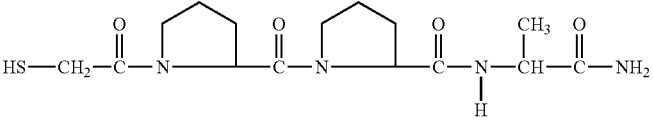 | 3400 |
| 2 | V | 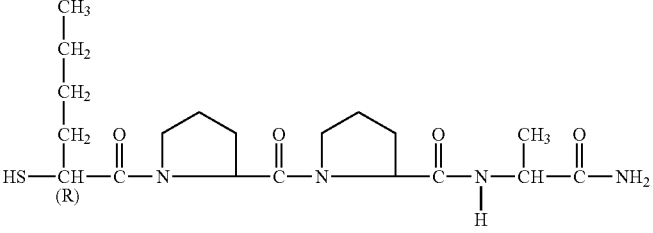 | 130 |
| 3 | VI | 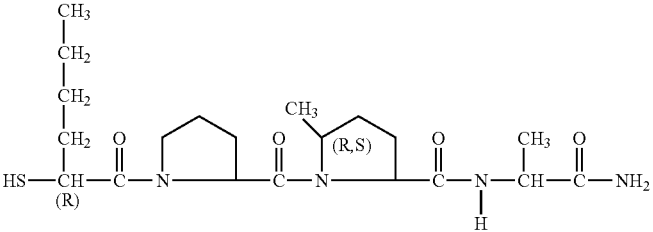 | 170 |
| 4 | VII | 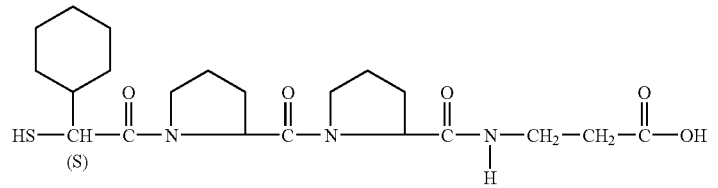 | 87 |
| 5 | VIII | 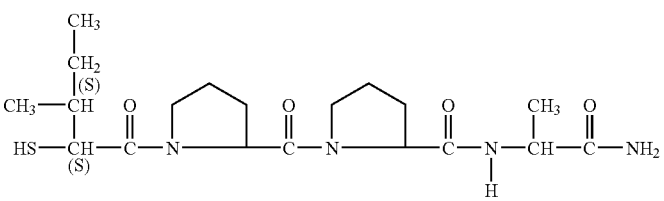 | 10 |

[1]The concentration (nmoles/liter) required to inhibit purified rat membrane aminopeptidase P by 50% using Arg-Pro-Pro (0.5 mM) as the substrate.

"Apstatin Analogue Inhibitors of Aminopeptidase P, a Bradykinin Degrading Enzyme," J. Med. Chem., 42, 2394-2402 (1999) at Tables 1-3 and the discussions thereof; and Ersahin et al., "Rat and Mouse Membrane Aminopeptidase P: Structure Analysis and Tissue Distribution," Arch. Biochem. Biophys., 417: 131-140 (2003) at FIG. 3 and the discussion thereof analyzing the rat-human correlation of Maggiora, et al., which are incorporated herein by reference. In particular, the relative potencies for the various mAPP inhibitors appears to be fairly constant regardless of the mammalian source of APP. Id. Moreover, rat mAPP approximates the relative predictability of monkey APP. Id.

As shown in Table 1 herein, the compounds of Formulas V-VIII have substantially improved (lower) $IC_{50}$s relative to the compound of Formula IV which lacks a second substituent on the α carbon atom containing the sulfhydryl (thio) substituent. In particular, adding a (second) hydrophobic substituent to the α carbon atom compound of Formula IV resulted in the $IC_{50}$ unexpectedly improving from 20 to 340 fold, i.e., from an $IC_{50}$ of 3400 nM to $IC_{50}$s ranging from 170 nM to 10 nM. In addition, varying the second substituent on the α carbon atom from n-butyl (Formula V) to iso-butyl (Formula VIII) resulted in an $IC_{50}$ that is 13 times lower. Thus, unexpectedly, the compound of Formula VIII is a 13 times more potent inhibitor of APP than its isomeric cousin of Formula V. It should also be pointed out that compounds V and VIII differ by having R and S stereochemistry at the α carbon atom.

In its second aspect, the present invention is directed to a pharmaceutical composition comprising in combination a therapeutically effective amount of the active compound of the present invention, as defined herein, and a pharmaceutically acceptable carrier. In one embodiment, the present invention is directed to a pharmaceutical composition comprising in combination a pharmaceutically acceptable carrier and a therapeutically acceptable amount of a compound of formula III:

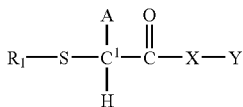

III wherein $C^1$ is of configuration S or R;
wherein $R_1$ is hydrogen, methyl, or

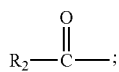

wherein A is a hydrogen, straight or branched chain lower alkyl having 1 to 8 carbon atoms, straight or branched chain lower alkenyl or alkynyl having 2 to 8 carbon atoms, cyclic alkyl or alkenyl having 4 to 8 carbon atoms, phenyl, or benzyl;
wherein X is (L)-prolyl, 3,4-dehydro-(L)-prolyl, (2S,3R)-3-methylpyrrolidine-2-carbonyl, (2S,5R)-5-methylpyrrolidine-2-carbonyl, (S)-piperidine-2-carbonyl, or (R)-thiazolidine-4-carbonyl;
wherein Y is an amino acid or a dipeptide, where in the dipeptide the first N-terminal amino acid is (L)-prolyl, 3,4-dehydro-(L)-prolyl, (2S,3R)-3-methylpyrrolidine-2-carbonyl, (2S,3S)-3-methylpyrrolidine-2-carbonyl, (2S,4R)-4-methylpyrrolidine-2-carbonyl, (2S,4S)-4-methylpyrrolidine-2-carbonyl, (2S,5R)-5-methylpyrrolidine-2-carbonyl, (2S,4R)-4-hydroxypyrrolidine-2-carbonyl, (2S,4S)-4-hydroxypyrrolidine-2-carbonyl, (S)-piperidine-2-carbonyl, or (R)-thiazolidine-4-carbonyl, and the second amino acid is (L)-alanyl, (L)-prolyl, sarcosyl, an (S, or R) N-methyl amino acid with a hydrophobic side chain, β-alanine, or other β-amino acid with a hydrophobic side chain, or a D-amino acid with a hydrophobic side chain; and wherein Y further has a carboxyl, carboxyamide, or a —$COOR_2$ moiety at its carboxyl terminus;
$R_2$ is alkyl or substituted alkyl having 1-6 carbon atoms, alkenyl or substituted alkenyl having 2-6 carbon atoms, cycloalkyl-$(CH_2)_a$—, aryl-$(CH_2)_a$—, substituted aryl-$(CH_2)_a$—, or heteroaryl-$(CH_2)_a$—; and a is zero or an integer from 1 to 6. Typically, a is 1 or 2. More typically, a is 1.

In another embodiment, the present invention is directed to a pharmaceutical composition comprising in combination, a pharmaceutically acceptable carrier and a therapeutically effective amount of a compound of Formula III:

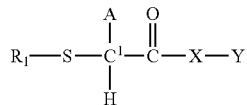

III wherein $C^1$ is of configuration S or R;
wherein $R_1$ is hydrogen or $R_2CO$—;
wherein A is straight or branched chain lower alkyl of 1-6 carbon atoms, ;
wherein X is (L) prolyl;
wherein Y is a dipeptide wherein the first (N-terminal) amino acid is (L) prolyl, and the second (C-terminal) amino acid is (L)-alanyl or β-alaninyl, or a one to six carbon alkyl- or aryl ester thereof; or (L)-alanyl amide or β-alaninyl amide;
$R_2$ is alkyl or substituted alkyl, having 1-6 carbon atoms; or cycloalkyl-$(CH_2)_a$—, aryl-$(CH_2)_a$—, substituted aryl-$(CH_2)_a$—, or heteroaryl-$(CH_2)_a$—, having 4-12 carbon atoms; and
a is zero or an integer from 1 to 2.

In yet another embodiment, the present invention is directed to a pharmaceutical composition comprising in combination, a pharmaceutically acceptable carrier and a therapeutically effective amount of a compound of Formula III:

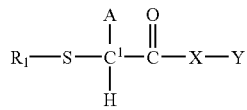

III wherein $C^1$ is of configuration S or R;
wherein $R_1$ is hydrogen or $R_2CO$—;
wherein A is straight or branched chain alkyl of 1-6 carbon atoms;
wherein X is (L) prolyl;
wherein Y is a dipeptide wherein the first (N-terminal) amino acid is (L) prolyl, and the second (C-terminal) amino acid is (L)-alanyl or β-alaninyl, or (L)-alanyl amide or β-alaninyl amide;
$R_2$ is alkyl or substituted alkyl, having 1-6 carbon atoms.

In a more preferred embodiment, the present invention is directed to a pharmaceutical composition comprising in combination a therapeutically effective amount of a compound of formula V, formula VI, formula VII or formula VIII in a pharmaceutically acceptable carrier.

In an even more preferred embodiment, the present invention is directed to a pharmaceutical composition comprising in combination a therapeutically effective amount of a compound of formula VIII:

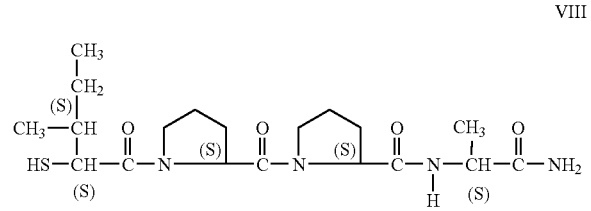

in a pharmaceutically acceptable carrier.

The term "therapeutically effective amount" as used herein means that amount of drug or pharmaceutical agent that will elicit the biological or medical response of a tissue, system or animal that is being sought by a researcher or clinician. An effective but nontoxic quantity of the compound is employed in treatment. The dosage regimen for preventing or treating symptoms by the compounds of this invention is selected in accordance with a variety of factors including the type, age, weight, sex, and medical condition of the mammal, the severity of the symptoms, the route of administration of the particular compound employed. An ordinary skilled physician or veterinarian will readily determine and prescribe the effective amount based on the route of administration of the agent to prevent or arrest the progress of the condition. In so proceeding, the physician or veterinarian employs relatively low dosages at first, subsequently increasing the dose until a maximum response is obtained.

In rats, bradykinin potentiation by apstatin has been observed with 0.08-0.8 mg/kg intravenously when administered over a one hour period. More potent inhibitors of the present invention, should be effective at five to tenfold lower dosages. See e.g., Table 1. Less potent inhibitors would require a greater dosage to provide the same therapeutic result. A typical therapeutically effective dose of a compound of the present invention is from about 0.008 mg/kg to 8.0 mg/kg, when given intravenously.

Regardless of the route of administration selected, a non-toxic but therapeutically effective quantity of one or more compounds of this invention is employed in any treatment. For preventing or treating a hypertensive condition or for treating a myocardial ischemia/reperfusion injury with the compounds of this invention, a dosage is selected in accordance with a variety of factors, including the type, age, weight, sex, and medical condition of the patient, the severity of the condition, the route of administration, and the particular compound employed in the treatment. A physician or veterinarian of ordinary skill can readily determine and prescribe the effective amount of the drug required to prevent or arrest the progress of the condition. In so proceeding, the physician or veterinarian could employ relatively low doses at first and subsequently increase the dose until a maximum response is obtained. Daily dosages of the compounds of the invention vary depending upon the $IC_{50}$ of the compound of the invention. However, oral dosages are ordinarily in the range of about 0.1 mg/kg up to about 200 mg/kg, (preferably, in the range of about 2.0 to 84.0 mg/kg (orally)).

The term "pharmaceutically acceptable carrier," as used herein, means a pharmaceutically-acceptable material, composition or vehicle, such as a liquid or solid filler, diluent, excipient, solvent or encapsulating material, involved in carrying or transporting a chemical agent, such as a compound of the present invention.

When combined with a pharmaceutically acceptable carrier, the compound of the present invention is suited for administration in oral dosage form as a tablet, capsule, softgel, pill, powder, granule, elixir, or syrup. The compounds may also be administered intravascularly, intraperitoneally, subcutaneously, intramuscularly, or topically using a liquid carrier form known to the pharmaceutical arts and as described below. Alternatively, the pharmaceutical composition of the present invention may be administered rectally or vaginally, in such forms as suppositories or bougies. In general, the preferred forms of the pharmaceutical composition are formulated for oral or intravenous administration, more preferably for oral administration.

For the orally administered pharmaceutical compositions and methods of the present invention, the foregoing active compounds described herein are typically provided in admixture with suitable pharmaceutical diluents, excipients, or carriers (collectively referred to herein as "carrier" materials) suitably selected with respect to the intended mode and form of administration, that is, oral tablets, capsules, softgels, elixirs, syrups, drops, and the like, and consistent with well known pharmaceutical practices.

For example, for oral administration in the form of a tablet or capsule, a therapeutically effective amount of one or more compounds of the present invention are combined with any oral non-toxic pharmaceutically acceptable inert carrier such as lactose, starch, sucrose, cellulose, magnesium stearate, dicalcium phosphate, calcium sulfate mannitol, and the like, or various combinations thereof. For oral administration in liquid forms, such as in softgels, elixirs, syrups, drops and the like, a therapeutically effective amount of the active drug components is combined with any oral non-toxic pharmaceutically acceptable inert carrier such as water, saline, ethanol, polyethylene, glycol, propylene glycol, corn oil, cottonseed oil, peanut oil, sesame oil, benzyl alcohol, various buffers, and the like, or a combination thereof. When desired or necessary, suitable binders, lubricants, disintegrating agents, and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes, or combinations thereof. Lubricants for use in these dosage forms include boric acid, sodium benzoate, sodium acetate, sodium chloride, and the like, or combinations thereof. Disintegrators include, without limitation, starch, methylcellulose, agar, bentonite, guar gum, and the like, or combinations thereof. Sweetening and flavoring agents and preservatives can also be included where appropriate.

For intravascular, intraperitoneal, subcutaneous, or intramuscular administration, one or more compounds of the present invention are combined with a suitable carrier such as water, saline, aqueous dextrose, and the like. For topical administration, one or more compounds of the present invention can be combined with pharmaceutically acceptable creams, oils, waxes, gels and the like. Regardless of the route of administration selected, the compounds of the present invention are formulated into pharmaceutically acceptable dosage forms by conventional methods known to those skilled in the art. The compounds may also be formulated using pharmacologically acceptable base addition salts. Moreover, the compounds or their salts may be used in a suitable hydrated form.

By virtue of their activity as mAPP antagonists, the compounds of Formula III are useful in inhibiting the breakdown of bradykinin (Bk), which in turn has the beneficial effects of decreasing blood pressure, dilating the coronary arteries, reducing cardiac ischemia/reperfusion injury, stimulating the formation of new blood vessels, and increasing renal perfusion and function. As a result, the compounds of the present invention are useful as the active agent in a pharmaceutical composition for inhibiting the breakdown of bradykinin, for treating hypertension, for treating myocardial ischemia/reperfusion injury, or for enhancing renal function in a mammalian patient, preferably a human patient. A physician or veterinarian of ordinary skill can readily determine whether a patient exhibits hypertension, myocardial ischemia, or diminished renal function. The preferred utility relates to reduction of ischemia/reperfusion injury.

Thus, in its third aspect, the present invention is directed to a method of inhibiting bradykinin degradation in a mammalian patient, preferably a human patient, in need of treatment comprising administering to the patient a therapeutically effective amount of a an APP inhibitor (compound) of the present invention in a first pharmaceutically effective carrier.

In another aspect, the present invention is directed to a method for treating hypertension in a mammalian patient, preferably a human patient, in need of treatment comprising administering to the patient a therapeutically effective amount of a compound of the present invention in a first pharmaceutically acceptable carrier.

In yet another aspect, the present invention is directed to a method for dilating the coronary arteries in a mammalian patient, preferably a human patient, in need of treatment comprising administering to the patient a therapeutically effective amount of a compound of the present invention in a first pharmaceutically acceptable carrier.

In yet another aspect, the present invention is directed to a method for treating cardiac ischemia/reperfusion injury in a mammalian patient, preferably a human patient, in need of treatment comprising administering to the patient a therapeutically effective amount of a compound of the present invention in a first pharmaceutically acceptable carrier.

In yet another aspect, the present invention is directed to a method for enhancing renal function in a mammalian patient, preferably a human patient, in need of treatment comprising administering to the patient a therapeutically effective amount of an compound of the present invention in a first pharmaceutically acceptable carrier.

In a second embodiment of each the above methods, the method includes the step of administering to said patient a therapeutically effective amount of an inhibitor of angiotensin converting enzyme in a second pharmaceutically acceptable carrier. The first pharmaceutically acceptable carrier for the compound (APP inhibitor) of the present invention, and the second pharmaceutically acceptable carrier for the inhibitor of ACE may be the same or different.

By the term "coadministering" as used herein, is meant that the aminopeptidase P inhibitor of the present invention and the ACE inhibitor be administered such that both are present in the patient's bloodstream at the same time in therapeutically effective amounts.

Thus, it is within the scope of the present invention that both compounds be administered as a single tablet, substantially simultaneously as two tablets, or in other instances, such as where one of the inhibitors has a long half-life in vivo, it may be sufficient that the two compounds be administered within the same forty-eight hour period. Preferably, the pharmaceutical composition of the present invention is administered in unit dosage form. However, regardless of how or when the inhibitors to APP and ACE are administered, the method of the present invention is directed to administering them such that the patient in need of treatment has a therapeutically effective amount of each member of the combination in their bloodstream at any particular time.

An effective but nontoxic quantity of the compound of the present invention is employed in any treatment. The dosage regimen for inhibiting bradykinin (Bk) degradation by the compound of this invention is selected in accordance with a variety of factors including the type, age, weight, sex and medical condition of the mammal, the severity of the symptoms, and the route of administration of the particular compound employed. A physician or veterinarian of ordinary skill will readily determine and prescribe the therapeutically effective dosage based on the route of administration of the Bk inhibitor to prevent or arrest the progress of the condition. In so proceeding, the physician or veterinarian would employ relatively low dosages at first, subsequently increasing the dose until a maximum response is obtained. Because the compounds of the present invention are excreted through the kidney, patients with impaired renal function would receive a lesser dose than patients with normal renal function. Physicians would assess a patient's renal function by monitoring the patient's serum creatinine. Serum creatinine concentrations increasing above 1.0 mg/dl reflect decreasing renal function. Thus, by the term "therapeutically effective amount" as used herein is meant the amount of the compound that is effective to cause substantial inhibition of its respective enzyme such that the combination substantially increases the half-life of any endogenous Bk that is formed in the patient.

Inhibitors of ACE are well known in the art and are used for inhibiting the in vivo conversion of angiotensin I to angiotensin II. Typical inhibitors of ACE include captopril, enalapril, enalaprilat, lisinopril, quinapril, benazepril, fosinopril, ramipril and ramiprilat. The method of administration and dosages for each of these ACE inhibitors is well known in the art and are disclosed in the 1995 Physician's Desk Reference.

In this method of the present invention, a physician or veterinarian would coadminister the ACE inhibitor component of the present invention at the above described dosages, allowing for variations due to the patient's weight, health, age, and renal condition. For example, serum creatinine concentration increasing above 1.0 mg/dl reflect decreasing renal function and a decreased ability to excrete the inhibitors used in the method of the present invention. However, in each instance, the patient is administered therapeutically effective amount, i.e., an amount sufficient to substantially inhibit the cleavage of Bk by ACE, and to substantially inhibit the cleavage of Bk in vivo when administered in conjunction with an inhibitor of aminopeptidase P as already discussed above.

In a second embodiment of the above described methods, the inhibitor of ACE is typically one or more members selected from the group of inhibitors of ACE consisting of captopril, enalapril, enalaprilat, lisinopril, quinapril, benazepril, fosinopril, ramipril and ramiprilat. Preferably, the inhibitor of ACE is one or more members selected from the group of inhibitors of ACE consisting of ramipril and ramiprilat.

The method of administration and dosages for each of these ACE inhibitors is well known in the art and are disclosed in the 1995 Physician's Desk Reference.

Captopril, which is also known as 1-[(2S)-3-mercapto-2-methyl propionyl]-L-proline, is typically administered to humans as tablets at between 18.75 mg to 150 mg/day with a target of 150 mg/day, but never to exceed 450 mg/day. Enalapril, which is also known as (S)-1-[N-[1-(ethoxycarbonyl)-3-phenylpropyl)]-L-alanyl]-L-proline, (Z) maleate (1:1), is typically administered to human patients as tablets at between 10 mg/day to 25 mg/day, not to exceed 50 mg/day. Enalapril is converted in vivo to enalaprilat, the acid form enalapril. Enalaprilat has the formula: (S)-1-[N-(1-carboxy-3-phenyl-propyl)-L-alanyl]-L-proline dihydrate and is typically administered intravenously. Lisinopril, which is also known as (S)-1-[$N^2$-(1-carboxy-3-phenylpropyl)-L-lysyl]-L-proline dihydrate, is typically administered to human patients as tablets at a dosage of 20 mg/day to 40 mg/day. Ramipril, which is also known as (2S,3aS,6aS)-I[(S)-N-[(S)-1-carboxy-3-phenylpropyl]alanyl]octahydrocyclopenta[b]pyrrole-2-carboxylic acid, 1-ethylester, is converted in vivo to its aliacid form ramiprilat. Ramipril is administered as tablets with the typical dosage for human patients of 2.5 mg/day to 20 mg/day.

EXAMPLE 1

Preparation of N-mercaptoacetyl-Pro-Pro-Ala-$NH_2$

Mercaptoacetyl-L-prolyl-L-prolyl-L-alaninamide (also known as N-mercaptoacetyl-Pro-Pro-Ala-$NH_2$ using the terminology for the other examples) is prepared by standard automated $N^\alpha$-(9-fluorenyl)methyloxycarbonyl (Fmoc)-solid phase peptide synthesis (see Chan, W. C. and White, P. D. (Eds.), Fmoc Solid Phase Peptide Synthesis: A Practical Approach, Oxford University Press, New York, N.Y. (2000)) starting with Fmoc-L-Ala-Rink amide-4-methylbenzhydrylamine resin. Residues are added to the resin by sequential deprotection/coupling cycles carried out in the following order: Fmoc-L-Pro, Fmoc-L-Pro, S-tritylmercaptoacetic acid (Peptides International, Louisville, Ky., Cat. No. ASX-5048-PI). Final cleavage of the peptide amide from the resin and removal of the trityl group is carried out simultaneously by treatment of the resin with 95% trifluoroacetic acid/scavenger. The resulting product, mercaptoacetyl-L-prolyl-L-prolyl-L-alaninamide, is purified by HPLC.

EXAMPLE 2

Preparation of N-[(R)-2-mercaptohexanoyl]-Pro-Pro-Ala-$NH_2$

The compound of Formula V, N-[(R)-2-mercaptohexanoyl]-Pro-Pro-Ala-$NH_2$, was commercially prepared by AnaSpec Inc., San Jose, USA as a contract synthesizer. A method for synthesis is described below.

A. Preparation of (S)-2-bromohexanoic acid (S)-2-aminohexanoic acid (FW 131.2, also known as L-norleucine) (1 g, 7.62 mmol), which is commercially available from Sigma Chemical Co at Sigmaaldrich.com, is dissolved in a mixture of HBr 48% (7.0 mL, 61 mmol) and $H_2O$ (10 mL). At 0° C., a solution of $NaNO_2$ (1.7 g, 24 mmol) in $H_2O$ (5 mL) is added over a period of 30 min. The reaction is stirred for two hours. The reaction mixture is degassed in vacuo and extracted with EtOAc (2×20 mL). The extracts are washed with water (15 mL), dried ($Na_2SO_4$), filtered and evaporated to give (S)-2-bromohexanoic acid.

B. Preparation of (R)-2-acetylthiohexanoic acid (S)-2-bromohexanoic acid (FW 195, 1.15 g, 5.9 mmol) from Example 2A is dissolved in dimethylformamide (DMF) (20 mL), and a solution of $CH_3COSK$ (1.01 g, 8.85 mmol) in DMF (10 mL) is added at 0° C. under nitrogen atmosphere. The reaction mixture is stirred for 2 hours and then evaporated. The residue is redissolved in EtOAc (35 mL), washed with 5% potassium bisulfate (15 mL) and water (15 mL) and 1N HCl (15 mL) and brine (15 mL), dried ($Na_2SO_4$), and evaporated to obtain (R)-2-acetylthiohexanoic acid.

C. Preparation of N-[(R)-2-acetylthiohexanoyl]-Pro-Pro-Ala-$NH_2$

To H-Pro-Pro-Ala-Rink amide resin (2.5 mmol, obtainable from AnaSpec Inc., San Jose, USA) in a reaction vessel with dimethylformamide (DMF) (40 mL), is added (R)-2-acetylthiohexanoic acid (FW 190, 1.06 g, 5.6 mmol) from Example 2B, diisopropylcarbodiimide (DIC) (880 µL, 5.6 mmol), 1-hydroxybenzotriazole (HOBt) (756 mg, 5.6 mmol), and diisopropylethylamine (DIEA) (974 µL, 5.6 mmol). After shaking overnight at room temperature, a ninhydrin test will show that coupling is complete. The resin is washed with DMF (3×30 mL) and dichloromethane (DCM) (3×30 mL), and then cleaved with trifluoroacetic acid (TFA) (50 mL) for 2 hours at room temperature. The resin is removed by filtration under reduced pressure and washed with TFA (2×10 mL). The filtrates are combined and concentrated on a rotary evaporator to a glassy film below 30° C. Cold diethyl ether (20 mL) is added to precipitate the peptide. The peptide is collected by filtration and washed with cold ether (2×5 mL). After drying, the crude title peptide is obtained.

D. Preparation of N-[(R)-2-mercaptohexanoyl]-Pro-Pro-Ala-$NH_2$

The crude N-[(R)-2-acetylthiohexanoyl]-Pro-Pro-Ala-$NH_2$ is dissolved in degassed THF (50 mL), and 1N NaOH (10 mL) is added at 0° C. under $N_2$ atmosphere. The reaction mixture is stirred for 4 hours at room temperature. After acidification with 2 N HCl to pH 4, the solvent is evaporated. The residue is purified using preparative reverse phase HPLC with a C-18 column, eluting with a water (containing 0.1% TFA)-acetonitrile gradient, where the gradient runs from 15%-55% acetonitrile over 60 minutes. The column fractions are analyzed by analytical HPLC and fractions containing product (purity >95%) are pooled and lyophilized to yield the title peptide.

EXAMPLE 3

Preparation of N-[(R)-2-mercaptohexanoyl]-Pro-MePro-Ala-$NH_2$

The compound of Formula VI, N-[(R)-2S,5RS)-5-methylpyrrolidine-2-carbonyl]-Ala-$NH_2$, as titled above, was commercially prepared by AnaSpec Inc., San Jose, USA as a contract synthesizer. A method for synthesis is described below.

A. Preparation of (S)-2-bromohexanoic acid (S)-2-aminohexanoic acid (FW 131.2, also known as L-norleucine) (1 g, 7.62 mmol), which is commercially available from Sigma Chemical Co at Sigmaaldrich.com, is dissolved in a mixture of HBr 48% (7.0 mL, 61 mmol) and $H_2O$ (10 mL). At 0° C., a solution of $NaNO_2$ (1.7 g, 24 mmol) in $H_2O$ (5 mL) is added over a period of 30 min. The reaction is stirred for two hours. The reaction mixture is degassed in vacuo and extracted with EtOAc (2×20mL). The extracts are washed with water (15 mL), dried ($Na_2SO_4$), filtered and evaporated to give (S)-2-bromohexanoic acid.

B. Preparation of (R)-2-acetylthiohexanoic acid (S)-2-bromohexanoic acid (FW 195, 1.15 g, 5.9 mmol) from Example 3A is dissolved in DMF (20 mL), and a solution of $CH_3COSK$ (1.01 g, 8.85 mmol) in DMF (10 mL) is added at 0° C. under nitrogen atmosphere. The reaction mixture is stirred for 2 hours and then evaporated. The residue is redissolved in EtOAc (35 mL), washed with 5% potassium bisulfate (15 mL) and water (15 mL) and 1N HCl (15 mL) and brine (15 mL), dried (Na$_2$SO$_4$), and evaporated to obtain (R)-2-acetylthiohexanoic acid.

C. Preparation of N-[(R)-2-acetylthiohexanoyl]-Pro-MePro-Ala-NH$_2$

To H-Pro-MePro-Ala-Rink amide resin (2.5 mmol, obtainable from AnaSpec Inc., San Jose, USA) in a reaction vessel with dimethylformamide (DMF) (40 mL), is added (R)-2-acetylthiohexanoic acid (FW 190, 1.06 g, 5.6 mmol) from Example 3B, diisopropylcarbodiimide DIC (880 µL, 5.6 mmol), 1-hydroxybenzotriazole (756 mg, 5.6 mmol), and diisopropylethyl amine (974 µL, 5.6 mmol). After shaking overnight at room temperature, a ninhydrin test will show that coupling is complete. The resin is washed with DMF (3×30 mL) and dichloromethane (3×30 mL), and then cleaved with trifluoroacetic acid (50 mL) for 2 hours at room temperature. The resin is removed by filtration under reduced pressure and washed with TFA (2×10 mL). The filtrates are combined and concentrated on a rotary evaporator to a glassy film below 30° C. Cold diethyl ether (20 mL) is added to precipitate the peptide. The peptide is collected by filtration and washed with cold ether (2×5 mL). After drying, the crude title peptide is obtained.

D. Preparation of N-[(R)-2-mercaptohexanoyl]-Pro-MePro-Ala-NH$_2$

The crude N-[(R)-2-acetylthiohexanoyl]-Pro-MePro-Ala-NH$_2$ is dissolved in degassed THF (50 mL), and 1N NaOH (10 mL) is added at 0° C. under N$_2$ atmosphere. The reaction mixture is stirred for 4 hours at room temperature. After acidification with 2 N HCl to pH 4, the solvent is evaporated. The residue is purified using preparative reverse phase HPLC with a C-18 column, eluting with a water (containing 0.1% TFA)-acetonitrile gradient, where the gradient runs from 15%-55% acetonitrile over 60 minutes. The column fractions are analyzed by analytical HPLC and fractions containing product (purity>95%) are pooled and lyophilized to yield the title peptide.

EXAMPLE 4

Preparation of N-[(S)-2-mercapto-2-cyclohexylacetyl]-Pro-Pro-β-Ala-OH

The compound of Formula VII, N-[(S)-2-mercapto-2-cyclohexylacetyl]-Pro-Pro-β-Ala-OH, was prepared as described below.

A. Preparation of (R)-2-bromo-2-cyclohexylacetic acid

The (R)-2-amino-2-cyclohexylacetic acid (H-Cyclohexyl-D-Gly-OH, 1 g, 6.36 mmol), which is commercially available from Bachem California Inc., Torrance, Calif. 90505, was dissolved in a mixture of HBr 48% (5.8 niL, 50.9 mmol) and H$_2$O (20 mL). At 0° C., a solution of NaNO$_2$ (1.4 g, 20.4 mmol) in H$_2$O (10 mL) was added over a period of 30 min. The reaction was stirred for two hours. The reaction mixture was degassed in vacuo and extracted with EtOAc (2×2mL). The extracts were washed with water (15 mL), dried (Na$_2$SO$_4$), filtered and evaporated to give 1.3 g (92% yield) of the (R)-2-bromo-2-cyclohexylacetic acid as a white solid.

B. Preparation of (S)-2-acetylthio-2-cyclohexylacetic acid

The (R)-2-bromo-2-cyclohexylacetic acid (1.3 g, 5.9 mmol) from Example 4A was dissolved in DMF (20 mL), and a solution of CH$_3$COSK (1.01 g, 8.85 mmol) in DMF (10 mL) was added at 0° C. under nitrogen atmosphere. The reaction mixture was stirred for 2 hours and then evaporated. The residue was redissolved in EtOAc (35 mL), washed with 5% potassium bisulfate (15 mL) and water (15 mL) and 1N HCl (15 mL) and brine (15 mL), dried (Na$_2$SO$_4$), and evaporated to obtain 1.2 g of the (S)-2-acetylthio-2-cyclohexylacetic acid as a yellow oil.

C. Preparation of N-[(S)-2-acetylthio-2-cyclohexylacetyl]-Pro-Pro-β-Ala-OH

To H-Pro-Pro-β-Ala-HMP resin (2.5 mmol, obtained from AnaSpec Inc. San Jose, USA) in a reaction vessel with dimethylformamide (40 mL), was added (S)-2-acetylthio -2-cyclohexylacetic acid (1.2 g, 5.6 mmol) from Example 4B, diisopropylcarbodiimide (880 µL, 5.6 mmol), 1-hydroxybenzotriazole (756 mg, 5.6 mmol), and diisopropylethylamine (DIEA) (974 µL, 5.6 mmol). After shaking overnight at room temperature, the ninhydrin test showed that coupling was complete. The resin was washed with DMF (3×30 mL) and dichloromethane (3×30 mL), and then cleaved with trifluoroacetic acid (TFA) (50 mL) for 2 hours at room temperature. The resin was removed by filtration under reduced pressure and washed with TFA (2×10 mL). The filtrates were combined and concentrated on a rotary evaporator to a glassy film below 30° C. Cold diethyl ether (20 mL) was added to precipitate the peptide. The peptide was collected by filtration and washed with cold ether (2×5 mL). After drying, 710 mg of the crude title peptide was obtained.

D. Preparation of N-[(S)-2-mercapto-2-cyclohexylacetyl]-Pro-Pro-β-Ala-OH

The crude N-[(S)-2-acetylthio-2-cyclohexylacetyl]-Pro-Pro-β-Ala-OH (710 mg) was dissolved in degassed THF (50 mL), and 1N NaOH (10 mL) was added at 0° C. under N$_2$ atmosphere. The reaction mixture was stirred for 4 hours at room temperature. After acidification with 2 N HCl to pH 4, the solvent was evaporated. The residue (620 mg) was purified using preparative reverse phase HPLC with a C-18 column, eluting with a water (containing 0.1% TFA)-acetonitrile gradient, where the gradient ran from 15%-55% acetonitrile over 60 minutes. The column fractions were analyzed by analytical HPLC and fractions containing product (purity>95%) were pooled to yield 138 mg of the title peptide after lyophilization. Mass spectral analysis of this peptide revealed an M+H$^+$ peak at 440.5 and M+Na$^+$ peak at 462.7.

EXAMPLE 5

Preparation of N-[(2S, 3S)-2-mercapto-3-methylpentanoyl]-Pro-Pro-Ala-NH$_2$

The compound of Formula VIII, N-[(2S, 3S)-2-mercapto-3-methylpentanoyl]-Pro-Pro-Ala-NH$_2$, was prepared as described below.

A. Preparation of (2R, 3S)-2-bromo-3-methylpentanoic acid

The (2R,3S)-2-amino-3-methylpentanoic acid (D-allo-isoleucine, 1g, 7.62 mmol) was dissolved in a mixture of HBr 48% (6.95 mL, 61 mmol) and H$_2$O (10.5 mL). At 0° C., a solution of NaNO$_2$ (1.68 g, 24.4 mmol) in H$_2$O (5 mL) was added over a period of 30 min. The reaction was stirred for two hours. The reaction mixture was degassed in vacuo and extracted with EtOAc (2×20mL). The extracts were washed with water (15 mL), dried (Na$_2$SO$_4$), filtered and evaporated to give 1.3 g (87% yield) of the (2R, 3S)-2-bromo-3-methylpentanoic acid as a light yellow oil.

B. Preparation of (2S, 3S)-2-acetylthio-3-methylpentanoic acid

The (2R, 3S)-2-bromo-3-methylpentanoic acid (650 mg, 3.33 mmol) was dissolved in dimethylformamide (DMF) (10 mL), and a solution of CH₃COSK (571 mg, 5 mmol) in DMF (5 mL) was added at 0° C. under nitrogen atmosphere. The reaction mixture was stirred for 2 hours and then evaporated. The residue was redissolved in EtOAc (25 mL), washed with 5% potassium bisulfate (10 mL) and water (10 mL) and 1N HCl (10 mL) and brine (10 mL), dried (Na₂SO₄), and evaporated to obtain 600 mg of the (2S, 3S)-2-acetylthio-3-methylpentanoic acid as an oil.

C. Preparation of N-[(2S, 3S)-2-acetylthio-3-methylpentanoyl]-Pro-Pro-Ala-NH₂

To H-Pro-Pro-Ala-Rink amide resin (1.5 mmol, obtained from AnaSpec Inc. San Jose, USA) in a reaction vessel with DMF (20 mL), (2S, 3S)-2-acetylthio-3-methylpentanoic acid (600 mg, 3.3 mmol), diisopropylcarbodiimide (DIC) (518 μL, 3.3 mmol), 1-hydroxybenzotriazole (443 mg, 3.3 mmol), and diisopropylethylamine (DIEA) (574 μL, 3.3 mmol) were added. After shaking overnight at room temperature, the ninhydrin test showed that coupling was complete. The resin was washed with DMF (3×20 mL) and dichloromethane (3×20 mL), and then cleaved with TFA (30 mL) for 2 hours at room temperature. The resin was removed by filtration under reduced pressure and washed with TFA (2×10 mL). The filtrates were combined and concentrated on a rotary evaporator to a glassy film below 30° C. Cold ether (20 mL) was added to precipitate the peptide. The peptide was collected by filtration and washed with cold ether (2×5 mL). After drying, the crude title peptide (450 mg) was obtained.

D. Preparation of N-[(2S, 3S)-2-mercapto-3-methyl-pentanoyl]-Pro-Pro-Ala-NH₂

The crude N-[(2S, 3S)-2-acetylthio-3-methylpentanoyl]-Pro-Pro-Ala-NH₂ (450 mg, ~1 mmol) was dissolved in degassed THF, and 1N NaOH (7 mL) was added at 0° C. under N₂ atmosphere. The reaction mixture was stirred for 4 hours at room temperature. After acidification with 2 N HCl to pH 4, the solvent was evaporated. The residue was purified using preparative reverse phase HPLC with a C-18 column, eluting with a water (containing 0.1% TFA)-acetonitrile gradient, where the gradient ran from 10%-35% acetonitrile over 60 minutes. The column fractions were analyzed by analytical HPLC and fractions containing product were pooled to yield 133 mg of the title peptide after lyophilization. Mass spectral analysis of this peptide revealed an M+H⁺ peak at 413.5 and M+Na⁺ peak at 435.6.

The invention claimed is:

1. A compound of formula III:

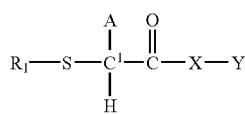

wherein $C^1$ is of configuration S or R;

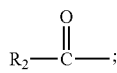

wherein $R_1$ is hydrogen, methyl, or wherein A is a hydrogen, straight or branched chain lower alkyl having 1 to 8 carbon atoms, straight or branched chain lower alkenyl or alkynyl having 2 to 8 carbon atoms, cyclic alkyl or ailcenyl having 4 to 8 carbon atoms, phenyl, or benzyl;

wherein X is (L)-prolyl, 3,4-dehydro-(L)-prolyl, (2S, 3R)-3-methylpyrrolidine-2-carbonyl, (2S, 5R)-5-methylpyrrolidine-2-carbonyl, (S)-piperidine-2-carbonyl, or (R)-thiazolidine-4-carbonyl;

X is connected to the carbonyl carbon of Formula III by a peptide bond;

wherein Y is a dipeptide, where in the dipeptide the first (N-terminal) amino acid is (L)-prolyl, 3,4-dehydro-(L)-prolyl, (2S, 3R)-3-methylpyrrolidine-2-carbonyl, (2S, 3S)-3-methylpyrrolidine-2-carbonyl, (2S, 4R)-4-methylpyrrolicline-2-carbonyl, (2S, 4S)-4-methylpyrrolidine-2-carbonyl, (2S, 5R)-5-metbylpyrrolidine-2-carbonyl, (2S, 4R)-4-hydroxypyrrolidine-2-carbonyl, (2S, 4S)-4-hydroxypyrrolidine-2-carbonyl, (S)-piperidine-2-carbonyl, or (R) -thiazolidine-4-carbonyl, and the second (C-terminal) amino acid is (L)-alanyl, (L)-prolyl, sarcosyl, an (S, or R) N-methyl amino acid with a hydrophobic side chain, β-alanine, or other β-amino acid with a hydrophobic side chain, or a D-amino acid with a hydrophobic side chain; the dipeptide Y is connected to X by a peptide bond; and wherein Y further has a carboxyl, carboxyamide, or a —COOR₂ moiety at its carboxyl terminus;

wherein $R_2$ is alkyl or substituted alkyl, having 1-6 carbon atoms; or cycloalkyl-$(CH_2)_a$—, aryl-$(CH_2)_a$—, substituted aryl-$(CH_2)_a$—, or heteroaryl-$(CH_2)_a$—, having 4-12 carbon atoms; and a is zero or an integer from 1 to 6.

2. The compound of claim 1, wherein $C^1$ is of configuration S or R;

wherein $R_1$ is hydrogen or $R_2CO$—;

wherein A is straight or branched chain alkyl of 1-6 carbon atoms, or cyclic alkyl or alkenyl having 4 to 8 carbon atoms;

wherein X is (L) prolyl;

wherein Y is a dipeptide wherein the first (N-terminal) amino acid is (L) prolyl, and the second (C-terminal) amino acid is (L)-alanyl or β-alaninyl, or a one to six carbon alkyl- or aryl ester thereof; or (L)-alanyl amide or β-alaninyl amide;

$R_2$ is alkyl or substituted alkyl, having 1-6 carbon atoms; or cycloalkyl-$(CH_2)_a$—, aryl-$(CH_2)_a$—, substituted aryl-$(CH_2)_a$—, or heteroaryl-$(CH_2)_a$—, having 4-12 carbon atoms; and a is zero or an integer from 1 to 6.

3. The compound of claim 2, wherein $C^1$ is of configuration S or R;

wherein $R_1$ is hydrogen or $R_2CO$—;

wherein A is straight or branched chain alkyl of 1-6 carbon atoms;

wherein X is (L) prolyl;

wherein Y is a dipeptide wherein the first (i.e., N-terminal) amino acid is (L) prolyl, and the second (i.e., C-terminal) amino acid is (L)-alanyl or β-alaninyl, or (L)-alanyl amide or β-alaninyl amide; and $R_2$ is alkyl or substituted alkyl, having 1-6 carbon atoms.

4. The compound of claim 1 selected from the group consisting of:

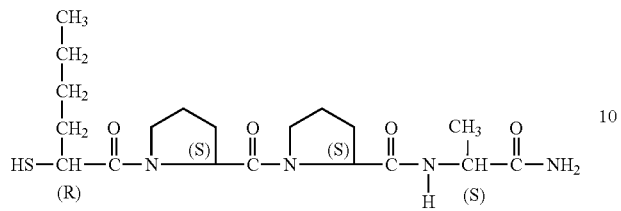

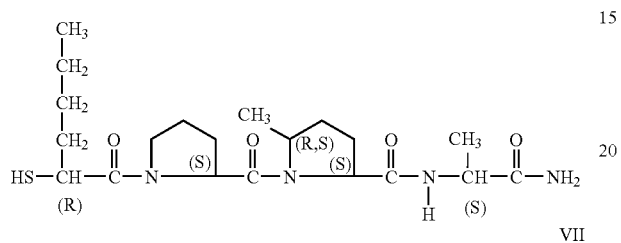

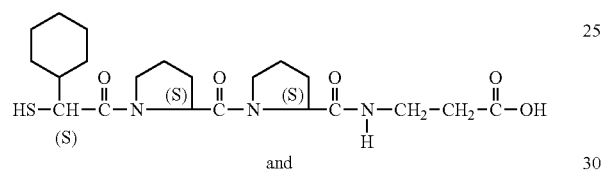

and

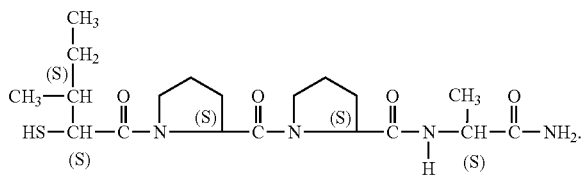

5. The compound of claim 4, wherein the compound is of Formula VIII.

6. A pharmaceutical composition comprising in combination a therapeutically effective amount of a compound of Formula III:

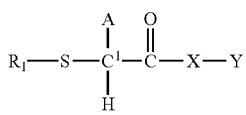

wherein $C^1$ is of configuration S or R;
wherein $R_1$ is hydrogen, methyl, or

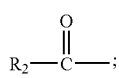

wherein A is a hydrogen, straight or branched chain lower alkyl having 1 to 8 carbon atoms, straight or branched chain lower alkenyl or alkynyl having 2 to 8 carbon atoms, cyclic alkyl or alkenyl having 4 to 8 carbon atoms, phenyl, or benzyl;

wherein X is (L)-prolyl, 3,4-dehydro-(L)-prolyl, (2S, 3R)-3-methylpyrrolidine-2-carbonyl, (2S, 5R)-5-methylpyrrolidine-2-carbonyl, (S)-piperidine-2-carbonyl, or (R)-thiazolidine-4-carbonyl;

X is connected to the carbonyl carbon of Formula III by a peptide bond;

wherein Y is a dipeptide, where in the dipeptide the first (N-terminal) amino acid is (L)-prolyl, 3,4-dehydro-(L)-prolyl, (2S, 3R)-3-methylpyrrolidine-2-carbonyl, (2S, 3S)-4-methylpyrrolidine-2-carbonyl, (2S, 4R)-4-methylpyrrolidine-2-carbonyl, (2S, 4S)-4-methylpyrrolidine-2-carbonyl, (2S, 5R)-5-methylpyrrolidine-2-carbonyl, (2S, 4R)-4-hydroxypyrrolidine-2-carbonyl, (2S, 4S)-4-hydroxypyrrolidine-2-carbonyl, (S)-piperidine-2-carbonyl, or (R)-thiazolidine-4-carbonyl, and the second (C-terminal) amino acid is (L)-alanyl, (L)-prolyl, sarcosyl, an (S, or R) N-methyl amino acid with a hydrophobic side chain, β-alanine, or other β-amino acid with a hydrophobic side chain, or a D-amino acid with a hydrophobic side chain; the dipeptide Y is connected to X by a peptide bond; and wherein Y further has a carboxyl, carboxyamide, or a —COOR$_2$ moiety at its carboxyl terminus;

$R_2$ is alkyl or substituted alkyl, having 1-6 carbon atoms; or cycloalkyl-(CH$_2$)$_a$—, aryl-(CH$_2$)$_a$—, substituted aryl-(CH$_2$)$_a$—, or heteroaryl-(CH$_2$)$_a$—, having 4-12 carbon atoms; and a is zero or an integer from 1 to 6;

and a pharmaceutically acceptable carrier.

7. The pharmaceutical composition of claim 6,
wherein $C^1$ is of configuration S or R;
wherein $R_1$ is hydrogen or $R_2$CO—;
wherein A is straight or branched chain alkyl of 1-6 carbon atoms, or cyclic alkyl or alkenyl
having 4 to 8 carbon atoms;
wherein X is (L) prolyl;
wherein Y is a dipeptide wherein the first (N-terminal) amino acid is (L) prolyl, and the second (C-terminal) amino acid is (L)-alanyl or β-alaninyl, or a one to six carbon alkyl- or aryl ester thereof; or (L)-alanyl amide or β-alaninyl amide;
wherein $R_2$ is alkyl or substituted alkyl, having 1-6 carbon atoms; or cycloalkyl-(CH$_2$)$_a$—, aryl-(CH$_2$)$_a$—, substituted aryl-(CH$_2$)$_a$—, or heteroaryl-(CH$_2$)$_a$—, having 4-12 carbon atoms; and
a is zero or an integer from 1 to 6.

8. The pharmaceutical composition of claim 7, wherein $C^1$ is of configuration S or R;
wherein R, is hydrogen or $R_2$ CO—;
wherein A is straight or branched chain alkyl of 1-6 carbon atoms;
wherein X is (L) prolyl;
wherein Y is a dipeptide wherein the first (i.e., N-terminal) amino acid is (L) prolyl, and the second (i.e., C-terminal) amino acid is (L)-alaninyl or β-alaninyl, or (L)-alanyl amide or β-alaninyl amide; and
$R_2$ is alkyl or substituted alkyl, having 1-6 carbon atoms.

9. The pharmaceutical composition of claim 6, wherein the compound is selected from the group consisting of:

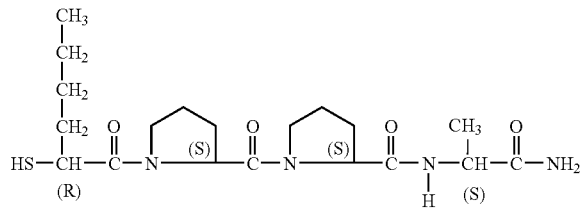
V

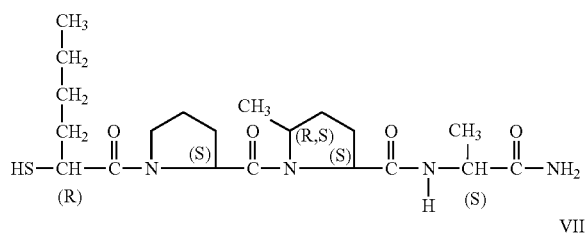
VI

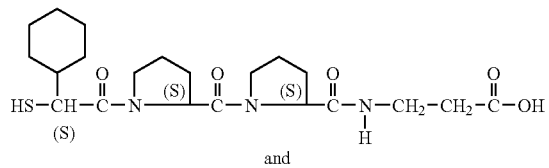
and
VII

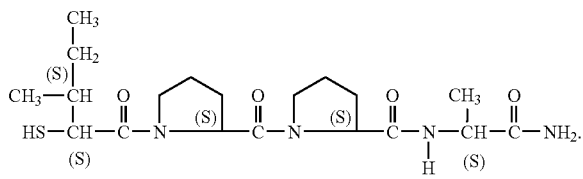
VIII

10. The pharmaceutical composition of claim 9, wherein the compound is of Formula VIII.

11. The pharmaceutical composition of claim 6 in the form of a tablet.

12. The pharmaceutical composition of claim 11, wherein the tablet is a softgel tablet.

13. The pharmaceutical composition of claim 8 in the form of a tablet.

14. The pharmaceutical composition of claim 13, wherein the tablet is a softgel tablet.

15. The pharmaceutical composition of claim 10 in the form of a tablet.

16. The pharmaceutical composition of claim 15, wherein the tablet is a softgel tablet.

17. The pharmaceutical composition of claim 6 in the form of an intravenous solution.

18. The pharmaceutical composition of claim 8 in the form of an intravenous solution.

19. The pharmaceutical composition of claim 10 in the form of an intravenous solution.

20. The pharmaceutical composition of claim 6, further comprising a therapeutically effective amount of an inhibitor of angiotensin converting enzyme (ACE).

21. The pharmaceutical composition of claim 8, further comprising a therapeutically effective amount of an inhibitor of angiotensin converting enzyme (ACE).

22. The pharmaceutical composition of claim 21, wherein said inhibitor of angiotensin converting enzyme is a member selected from the group consisting of captopril, enalapril, enalaprilat, lisinopril, quinapril, benazepril, fosinopril, ramipril, and ramiprilat.

23. The pharmaceutical composition of claim 22, wherein said inhibitor of angiotensin converting enzyme is captopril.

24. The pharmaceutical composition of claim 22, wherein said inhibitor of angiotenslin converting enzyme is enalapril.

25. The pharmaceutical composition of claim 22, wherein said inhibitor of angiotensin converting enzyme is enalaprilat.

26. The pharmaceutical composition of claim 22, wherein said inhibitor of angiotensin converting enzyme is lisinopril.

27. The pharmaceutical composition of claim 22, wherein said inhibitor of angiotensin converting enzyme is a member of the group consisting of ramnipril and ramiprilat.

* * * * *